United States Patent [19]

Carney et al.

[11] Patent Number: 4,877,899

[45] Date of Patent: Oct. 31, 1989

[54] NOVEL COMPOSITIONS

[75] Inventors: Robert L. Carney, Palo Alto; Thomas L. Brown, Modesto, both of Calif.

[73] Assignee: Sandoz Ltd., Basle, Switzerland

[21] Appl. No.: 554,733

[22] Filed: Nov. 23, 1983

[51] Int. Cl.$^4$ .............................................. C07C 67/02
[52] U.S. Cl. ................................... 560/262; 424/300; 424/301; 424/311; 424/312; 424/331; 424/337; 514/708; 514/710; 514/478; 514/512; 514/546; 514/552; 558/276; 558/275; 560/163; 560/165; 560/226; 560/228; 560/229; 560/254; 568/29; 568/31; 568/32; 568/33; 568/37; 568/39; 568/43; 568/45; 568/50; 568/55; 568/51; 260/399; 260/400; 260/402
[58] Field of Search ............... 560/262, 254, 163, 165, 560/226, 228, 229; 568/29, 31–33, 37, 39, 43, 45, 50, 55, 51; 260/399, 400, 402, 463, 465 D, 465 F; 424/300, 301, 311, 312, 331, 337; 514/708, 710, 546, 552, 478, 512; 558/276

[56] References Cited

U.S. PATENT DOCUMENTS

| | | | |
|---|---|---|---|
| 3,835,195 | 9/1974 | Menet | 568/32 |
| 4,219,667 | 8/1980 | Julia et al. | 568/32 |

FOREIGN PATENT DOCUMENTS

| | | | |
|---|---|---|---|
| 747234 | 9/1970 | Belgium | 568/37 |
| 2606624 | 9/1976 | Fed. Rep. of Germany | 568/55 |
| 2630947 | 2/1977 | Fed. Rep. of Germany | . |
| 2640790 | 3/1977 | Fed. Rep. of Germany | . |
| 9108 | 2/1977 | Netherlands | 568/32 |

OTHER PUBLICATIONS

CA 78:147563e, Manning R. E. (1973).
CA 85:159427w, Miyamoto, N. et al. (1976).
Schorstein et al., Latent Inhibition of Liver Alcohol Dehydrogenase by Subst. Allyl Alcohol., *J. C. S. Chem. Comm.*, 795 (1978).

Primary Examiner—Paul J. Killos
Attorney, Agent, or Firm—Jacqueline S. Larson

[57] ABSTRACT

Sulfur-substituted alkenyl compounds, synthesis thereof, intermediates therefor, and the use of the compounds to control pests.

20 Claims, No Drawings

NOVEL COMPOSITIONS

The present invention relates to sulfur-substituted alkenyl compounds, synthesis thereof, intermediates therefor, and the use of the compounds to control pests.

More particularly, the compounds of the present invention are represented by the following formula (A):

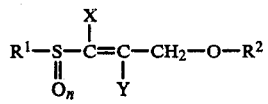
(A)

wherein,
n is zero, one or two;
$R^1$ is lower alkyl, lower haloalkyl, lower alkenyl, lower haloalkenyl, lower alkoxyalkyl, phenylalkyl or substituted phenylalkyl;
$R^2$ is hydrogen, lower alkyl, lower haloalkyl, lower alkoxyalkyl, lower acylalkyl, lower alkenyl, lower haloalkenyl, lower alkynyl, lower acyl, lower haloacyl, lower alkoxycarbonyl or lower alkylaminocarbonyl;
X is hydrogen, lower alkyl, lower haloalkyl or halogen; and
Y is hydrogen or halogen.

In the description hereinafter and the appended claims, each of n, $R^1$, $R^2$, X and Y is as defined hereinabove, unless otherwise specified.

The compounds of the present invention are further represented by the following embodiments (B), (C) and (D), which are encompassed by formula (A):

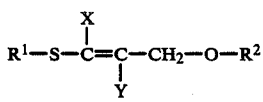
(B)

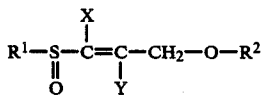
(C)

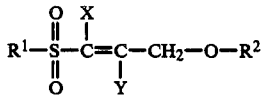
(D)

Certain of the compounds of the present invention are novel. Others are disclosed in German OLS 26 40 790, which teaches utility as bacteriocides.

The compounds of formula A exhibit an unexpected usefulness for the control of insects. The utility of these compounds as insect control agents is believed to be attributable to their anti-juvenile hormone activity. They are preferably applied to the immature insect, namely during the embryo, larval or pupal stage, in view of their effect on metamorphosis and otherwise abnormal development. These compounds can be effective control agents for insects of, for example, the orders Lepidoptera, Hemiptera, Homoptera, Coleoptera and Diptera, and other insects. The compounds can be applied to the insect or its locus in an insect controlling amount, usually of the order of 0.1 μg to 100 μg per insect.

In the use of the compounds of formula A for combatting insects, a compound of formula A, or mixtures thereof, can be combined with a carrier substance for application to the locus. The carrier can be liquid or solid and include adjuvants such as wetting agents, dispersing agents and other surface active agents. The compounds can be used in formulations such as wettable powders, solutions, dusts, granules, emulsifiable concentrates and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to 90.0 percent, by weight. Generally, a concentration of less than 25 percent of the active compound is employed. The compounds of the present invention can be used in combination with other pesticides such as the synthetic pyrethroids, carbamates and insect growth regulators, or with insect attractants.

The compounds of the present invention of formula A contain a carbon-carbon double bond and may exist as E and Z geometrical isomers. The present invention includes each of the geometric isomers and mixtures of the two.

The compounds of the present invention of formula C have an asymmetric sulfur atom. The present invention includes each of the optical isomers and racemic mixtures thereof. In the examples hereinafter, unless otherwise specified, the compound prepared is a racemic mixture.

The compounds of formula B can be prepared as outlined below:

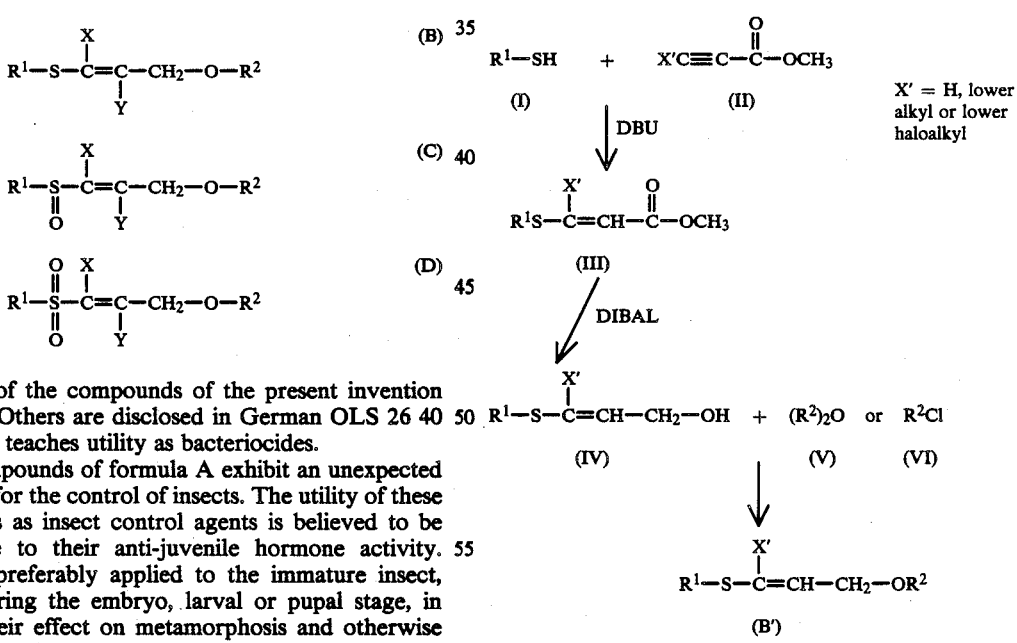

A thiol (I) and a methyl alkynoate (II; X' is hydrogen, lower alkyl or lower haloalkyl) are reacted together in the presence of a catalytic amount of 1,8-diazabicyclo[5.4.0]undec7-ene (DBU) to give a methyl thioalkenoate (III) as a mixture of Z and E isomers that may be separated chromatographically. The thioalkenoate (III) is then treated with diisobutylaluminum hydride (DIBAL) at a temperature below room temperature to give the corresponding alcohol (IV). The alcohol (IV)

is reacted with either $(R^2)_2O$ (V) or $R^2Cl$ (VI) to give the compound B' (B where X is hydrogen, lower alkyl or lower haloalkyl and Y is hydrogen).

Alternatively, the compounds of B' can be prepared the reaction of an allyl sulfide (XII) and t-butylhypochlor at a temperature below room temperature to give a thiopropeny chloride (XIII), which is then reacted with an alcohol $R^2OH$ at room temperature in the presence of a suitable base.

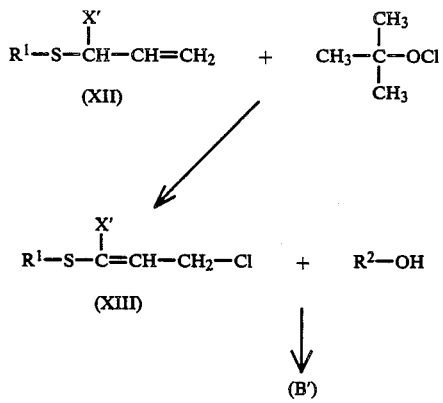

To prepare compounds of formula B" (B where X is halogen), a compound of formula B' where X' is hydrogen is reacted with, for example, silver fluoride and iodine, or with iodine monofluoride, iodine monochloride, iodine or bromine followed by treatment with triethylamine to give compound B".

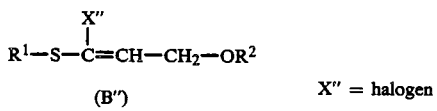

When X' is hydrogen, the compounds of formula IV can be prepared by the following alternative method:

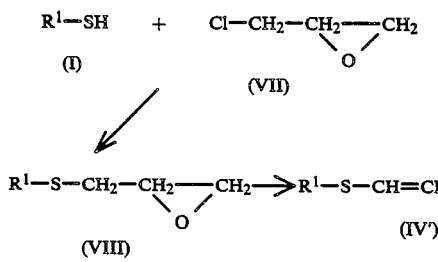

A thiol (I) is first treated with sodium hydroxide, then reacted with epichlorohydrin (VIII) at a temperature below room temperature followed by heating to elevated temperature to give the corresponding thiomethyloxirane (VIII). The thiomethyloxirane is reacted with a catalytic amount of potassium t-butoxide to give the thiopropenol (IV') as a mixture of the E and Z isomers. Alternatively, a bromide (IX) can be reacted with 3-mercapto-1,2-propanediol (X) in the presence of sodium hydride to give a thiohydroxypropanol (XI), which is then treated with tosyl chloride and pyridine followed by sodium hydroxide to give a thiomethyloxirane (VIII), which is then reacted with potassium t-butoxide as above.

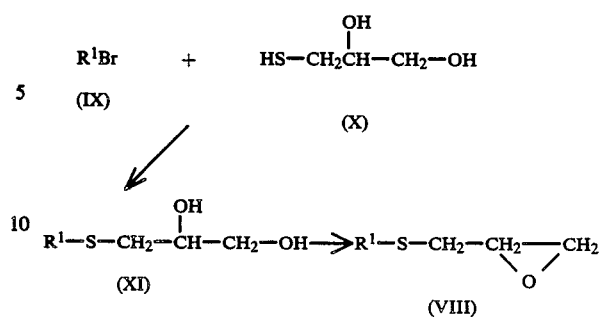

Alternatively, the thiohydroxypropanol (XI) where $R^1 = R^{1'}CHZ-CZ_2$ may be prepared by reacting 3-mercapto-1,2-propanediol (X) with a terminal olefin (XIV) at elevated temperature in the presence of a catalytic amount of a free radical initiator, such as azobisisobutyronitrile (AIBN).

$$R^{1'} = CZ=CZ_2 \quad (XIV)$$

Z = H or F
$R^{1'}$ = values of $R^1$ where the number of carbon atoms is not greater than six.

To prepare compounds of formula B where Y is halogen, a compound of formula B where Y is hydrogen is reacted with bromine, chloride, bromine monochloride or iodine monochloride, followed by DBU or another base.

To prepare compounds of formula B where both X and Y are halogen, a thiocyanate of formula (XV) is reacted with the dilithio derivative of propargyl alcohol to give a thioalkynol of formula (XVI), which is then reacted with either $(R^2)_2O$ or $R^2Cl$ to give a compound of formula (XVII). Reaction of chlorine, bromine monofluoride, bromine monochloride, bromine, iodine monofluoride or iodine monochloride with the compound (XVII) gives compound (B) where both X and Y are halogen.

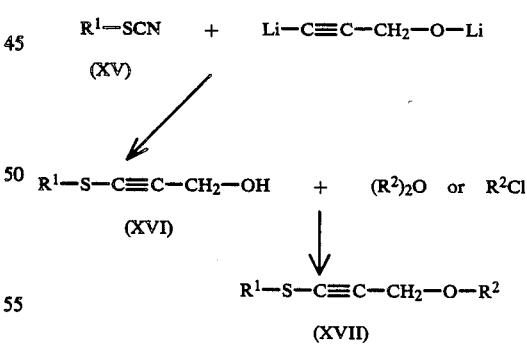

To prepare compounds of formula C, a thio compound of formula B is reacted with m-chloroperbenzoic acid to give the corresponding sulfinyl compound.

Likewise, to prepare compounds of formula,D, a compound of formula C is reacted with m-chloroperbenzoic acid to give the corresponding sulfonyl compound.

The following terms, wherever used in the description herein and in +h=appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkenyl" refers to an ethylenically unsaturated hydrocarbon group, straight or branched, having a chain length of two to eight carbon atoms and one or two ethylenic bonds. The term "lower haloalkenyl" refers to a lower alkenyl group substituted with one to three halogen atoms.

The term "lower alkynyl" refers to an alkynyl group, straight or branched, having a chain length of two to eight carbon atoms and one or two acetylenic bonds.

The term "phenylalkyl" refers to a lower alkyl group substituted with a phenyl group.

The term "substituted phenylalkyl" refers to a phenylalkyl group substituted at one, two or three of the ring carbon atoms with a group selected from lower alkyl, lower haloalkyl, lower alkoxy, lower haloalkoxy, lower alkenyl, lower haloalkenyl, lower alkenyloxy, halogen, nitro, cyano or lower alkylthio.

The term "lower alkoxyalkyl" refers to an alkyl group substituted at one of the carbon atoms by an alkoxy group, straight or branched, the total number of carbon atoms being not greater than ten.

The term "lower acyl" refers to an acyl group, straight or branched, having a chain length of two to eight carbon atoms. The term "lower haloacyl" refers to a lower acyl group substituted with one to three halogen atoms.

The term "lower acylalkyl" refers to a lower alkyl group substituted with a lower acyl group, the total number of carbon atoms being not greater than ten.

The term "lower alkoxycarbonyl" refers to a carbonyl group having attached thereto an alkoxy group, straight or branched, the total number of carbon atoms being not greater than eight.

The term "lower alkylaminocarbonyl" refers to a carbonyl group having attached thereto a mono- or dialkylamino group, straight or branched, the total number of carbon atoms being not greater than eight.

The following examples are provided to illustrate the practice of the present invention. Temperature is given in degrees Centigrade. The abbreviation "RT" refers to room temperature, approximately 23°.

EXAMPLE 1

To a cooled (5°) solution of methyl propiolate (1.96 g, 23.0 mmol) is added 2 drops of DBU. 1-Hexanethiol (2.5 g, 21.0 mmol) is then added over a period of 3 minutes. The ice bath is removed, and the reaction mixture is stirred at RT for 1.5 hours. It is then purified by prep. TLC (preparative thin layer chromatography) to give methyl 3-hexylthio-2-propenoate.

To a cooled (5°) solution of the above methyl 3-(hexylthio)-2-propenoate (0.84 g, 4.2 mmol) in 5 ml of hexane is added dropwise 10.7 ml (9.7 mmol) of a DIBAL solution (0.91 M/hexane). After addition is complete, the ice bath is removed. Aqueous methanol (3 ml MeOH:2 ml H$_2$O) is added dropwise, followed by ether, and the reaction mixture is filtered, washed with ether and then stripped of solvent to give 3-hexylthio-2-propenol.

To the above alcohol (0.64 g) is added 2 ml of pyridine, followed by 1 ml of acetic anhydride and the mixture is stirred at RT to give 3-hexylthio-2-propenyl acetate.

EXAMPLE 2

To a solution of 3-hexylthio-2-propenyl acetate (0.78 g, 3.6 mmol) in 20 ml of acetonitrile is added silver fluoride (1.83 g, 14.4 mmol) and the mixture is stirred at RT for 10 min. Iodine (1.14 g, 4.5 mmol) is then added, followed by stirring at RT for 15 min. Triethylamine (5 ml, 36.0 mmol) is added and the reaction mixture is stirred at RT overnight. It is then filtered and stripped of solvent. The residue is taken into chloroform and is filtered once more and concentrated. The crude product is purified by prep. TLC to give 3-fluoro3-hexylthio-2-propenyl acetate.

NMR (CDCl$_3$) δ4.85 - 5.85 (m, cis and trans CF=CH), 4.45 –4.72 (m, 2, CH$_2$O), 2.73 (m, 2, CH$_2$S-), 2.03

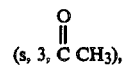

(s, 3, C CH$_3$), 1.32 (m, 8, (CH$_2$)$_4$), 0.87 (m, 3, CH$_3$).

EXAMPLE 3

To a solution of 3-fluoro-3-hexylthio-2-propenyl acetate (0.36 g, 1.5 mmol) in 5 ml of methylene chloride is added m-chloroperbenzoic acid (0.34 g, 1.7 mmol) at 5°. After the reaction is complete, the reaction mixture is diluted with methylene chloride, poured into aqueous saturated Na$_2$CO$_3$, extracted with methylene chloride (2X), washed with brine, dried and stripped of solvent to give 3-fluoro-3-hexylsulfinyl2-propenyl acetate. The product is purified by prep. TLC on silica gel eluting with 40% ethylacetate/hexane. The upper band is collected to give (E)-3-fluoro-3-hexylsulfinyl-2propenyl acetate (cpd. 1, Table A).

NMR (CDCl$_3$) δ5.82 (d of t, 1, J=35, J=6.8 Hz, trans CF=CH), 4.78 (d of d, 2, J=2.4, J=7.0 Hz, CH$_2$O), 2.95 (m, 2, CH$_2$S=O), 2.04 (s, 3, CH$_3$C=O), 1.37 (m, 8, (CH$_2$)$_4$), 0.95 (m, 3, CH$_3$).

The lower band is collected to give (Z)-3-fluoro-3-hexylsulfinyl-2-propenyl acetate.

NMR (CDCl$_3$) δ5.9 (d of t, 1, J=17, J=7.0 Hz, cis CF=CH), 4.8 (d of d, 2, J=2.0, J=9.0 Hz, CH$_2$O), 3.02 (m, 2, CH$_2$S=O), 2.02 (s, 3, CH$_3$C=O), 1.34 (m, 8, (CH$_2$)$_4$), 0.88 (m, 3, CH$_3$).

Following the above procedure, each of the (E) and (Z) isomers of 3-fluoro-3-hexylsulfinyl-2-propenyl acetate is reacted with m-chloroperbenzoic acid to yield, respectively, the (E) and (Z) isomer of 3-fluoro-3-hexylsulphonyl-2-propenyl acetate.

EXAMPLE 4

To a solution of (E)-3-fluoro-3-hexylsulfinyl-2propenyl acetate (3.0 g, 12.0 mmol) in 20 ml of methanol under N$_2$ is added aqueous sodium hydroxide (3.0 g, 37.5 mmol). After 30 min. at RT, the solution is diluted with water and extracted with ether. The aqueous phase is diluted with saturated brine and extracted again with ether. The combined ether extracts are dried over Na$_2$SO$_4$ and stripped to give (E)-3-fluoro-3-hexylsulfinyl-2-propenol (cpd. 2, Table A).

NMR (CDCl$_3$) δ 5.89 (d of t, 1, J=36, J=6.8 Hz, trans CF=CH), 4.40 (d of d, 2, J=2.4, J=6.8 Hz, CH$_2$O), 2.92 (m, 2, CH$_2$S=O), 1.34 (m, 8, (CH$_2$)$_4$), 0.90 (t, 3, J=6.3 Hz, CH$_3$)

EXAMPLE 5

To a mixture of (E)-3-fluoro-3-hexylsulfinyl-2-propenol (0.21 g, 1.0 mmol) and 2 ml of pyridine cooled to −30° is added through syringe acetic-formic anhydride (0.4 ml). The mixture is allowed to warm to 10° over a period of 1 hour. It is then diluted with water, extracted with hexane, washed with aqueous 2N $H_2SO_4$, then water, then aqueous $NaHCO_3$, finally brine and is dried. The product is purified by prep. TLC to give (E)-3-fluoro-3-hexylsulfinyl-2-propenyl formate (cpd. 3, Table A).

NMR ($CDCl_3$) δ 8.05 (s, 1, HC=O), 5.87 (d of t, 1, J=35, J=6.8 Hz, trans CF=CH) 4.90 (d of d, 2, J=2.4, J=6.8 Hz, $CH_2O$), 2.92 (m, 3, $CH_2S$=O), 1.4 (m, 8, $(CH_2)_8$), 0.90 (m, 3, $CH_3$).

EXAMPLE 6

To a solution of (E)-3-fluoro-3-hexylsulfinyl-2-propenol (0.22 g, 1.06 mmol) in 1 ml of pyridine is added butyric anhydride (0.18 ml, 1.1 mmol). The mixture is stirred at RT for 15 hours, then is diluted with water and allowed to stand for 2 hours, followed by extraction with ether/hexane. The organic phase is washed with $KHCO_3$, stripped and purified by column chromatography on silica gel to give (E)-3-fluoro-3-hexylsulfinyl-2-propenyl butyrate (cpd. 4, Table A).

NMR ($CDCl_3$) δ 5.85 (d of t, 1, J=35, J=6.8 Hz, trans CF=CH), 4.85 (d of d, 2, J=2.4, J=6.8 Hz, $CH_2O$), 2.92 (m, 2, $CH_2S$=O), 2.32 (t, 2, J=6.8 Hz, $CH_2C$=O), 1.35 (m, 10, $(CH_2)_5$), 0.96 (2t, 6, J=7.0 Hz, 2 $CH_3$).

EXAMPLE 7

To a solution of (E)-3-fluoro-3-hexylsulfinyl-2-propenol (0.22 g, 1.06 mmol) in 1 ml of pyridine is added ethyl chloroformate (0.10 ml). A vigorous reaction ensues, with some $CO_2$ evolution. After 14 hours at RT, the mixture is diluted with water and ether. The ether phase is washed with saturated brine, stripped and purified by column chromatography to give the ethyl carbonic acid ester (cpd. 5, Table A).

NMR ($CDCl_3$) δ 5.90 (d of t, 1, J=35, J=6.8 Hz, trans CF=CH), 4.85 (d of d, 2, J=2.4, J=6.8 Hz, CF=CH-$CH_2O$) 4.22 (q, 2, J=7.2 Hz, $CH_3CH_2O$), 2.92 (m, 2, $CH_2S$=O), 1.32 (t, J=7.0 Hz, $OCH_2C\underline{H}_3$, 0.90 (t, 3, J=5.3 Hz, $(CH_2)_5C\underline{H}_3$).

EXAMPLE 8

Following the procedure of Example 1, 3-heptylthio-2-propenyl acetate is prepared from methyl propiolate, 1-heptanethiol and acetic anhydride.

The above acetate (1.5 g, 6.5 mmol) in 10 ml of acetonitrile is added to a vigorously stirred suspension of silver fluoride (3.3 g, 26.0 mmol) in chloroform. The mixture is stirred at RT for 10 min., after which time iodine (2.06 g, 8.0 mmol) is added. After stirring for 15 min, triethylamine (9.1 ml, 65.0 mmol) is added and stirring is continued for 2.5 hours. The reaction mixture is filtered, washed with chloroform and stripped of solvent. The residue is taken up in chloroform, filtered, stripped and purified by prep. TLC to give 3-fluoro-3-heptylthio-2-propenyl acetate.

NMR ($CDCl_3$) δ 4.9–5.9 (m, 1, cis and trans CF=CH), 4.5–4.75 (m, 2, $CH_2O$), 2.77 (m, 2, $CH_2S$), 2.08 (S, 3, $CH_3C$=O), 1.34 (m, 10, $(CH_2)_5$), 0.94 (m, 3, $CH_3$).

Following the procedure of Example 3, the above acetate (0.71 g, 2.86 mmol) is reacted with m-chloroperbenzoic acid to give 3-fluoro-3-heptylsulfinyl-2-propenyl acetate. The product is purified by prep. TLC on silica gel eluting with 40% ethyl acetate/hexane and the top band is collected to give (E)-3-fluoro-3-heptylsulfinyl-2-propenyl acetate (cpd. 6, Table A).

NMR ($CDCl_3$) δ 5.83 (d of t, 1, J=35, J=6.8 Hz, trans CF=CH), 4.79 (d of d, 2, J=6.8, J=2.4 Hz, $CH_2O$), 2.9 (m, 2, $CH_2S$), 2.09 (S, 3, $CH_3C$=O), 1.37 (m, 10, $(CH_2)_5$), 0.9 (m, 3, $CH_3$).

Following the above procedures, each of 3-butylthio-2-propenyl acetate and 3-pentylthio-2-propenyl acetate is prepared from 1-butanethiool 1-propanethiol, respectively, methylpropiolate and acetic anhydride. Each acetate is reacted with silver fluoride, followed by iodine and triethylamine to yield, respectively, 3-fluoro-3-butylthio-2-propenyl acetate, and 3-fluoro-3-pentylthio-2-propenyl acetate.

Each of the above acetates is reacted with m-chloroperbenzoic acid to give, following purification and collection of the upper band, (E)-3-fluoro-3-butylsulfinyl-2-propenyl acetate (cpd. 7, Table A), NMR ($CDCl_3$) δ 5.85 (d of t, 1, J=35, J=6.8 Hz, trans CF=CH), 4.8 (d of d, 2, J=2.4, J=7.0 Hz, $CH_2O$), 2.93 (m, 3, $CH_2S$=O), 2.1 (S, 3, $CH_3C$=O), 1.62 (m, 4, $(CH_2)_2$), 0.97 (m, 3, $CH_3$); and (E)-3-fluoro-3-pentylsulfinyl-2-propenyl acetate (cpd. 8, Table A), NMR ($CDCl_3$) δ 5.87 (d of t, 1, J=35, J=6.8 Hz, trans CF=CH), 4.79 (d of d, 2, J-2.4, J=7.0 Hz, $CH_2O$), 2.9 (m, 2, $CH_2S$=O), 2.03 (s, 3, CH C=O), 1.42 (m, 6, $(CH_2)_3$), 0.9 (m, 3, $CH_3$).

Likewise, each of the above sulfinyl compounds is treated with m-chloroperbenzoic acid to give (E)-3-fluoro-3-butylsulfonyl-2-propenyl acetate, NMR ($CDCl_3$) δ 6.2 (d of t, 1, J=32, J=6.4 Hz, trans CF=CH), 4.8 (d of d, 2, J=6.4 Hz, $CH_2O$), 3.14 (m, 2, $CH_2S$=O), 2.10 (S, 3, $CH_3C$=O), 1.63 (m, 4, $(CH_2)_2$), 0.96 (t, 3, J=6.0 Hz, $CH_3$); and (E)-3-fluoro-3-pentylsulfonyl-2-propenyl acetate.

EXAMPLE 9

Two drops of DBU is added to methyl 2-butynoate (6.0 g) under $N_2$. 1-Octanethiol (8.96 g, 61.2 mmol) is added dropwise over 20 min. with cooling with an ice bath. The mixture is allowed to come to RT and is stirred overnight. It is then diluted with ether, washed, dried and stripped and the product is purified by prep. TLC to give methyl (E)-3-octylthio-2butenoate.

The above butenoate (2 g) is dissolved in ether under $N_2$ and cooled to 0°. DIBAL (18.9 ml, 1M solution in hexane) is added by syringe over 1 min. The mixture is stirred with water, filtered and stripped to give (E)-3-octylthio-2-butenol.

The above butenol (1.32 g) is dissolved in 20 ml of dry ethyl acetate, and 0.58 ml of pyridine is added in one portion. The mixture is cooled in an ice water bath and acetyl chloride (0.53 g) is added by syringe over 30 seconds. The mixture is then allowed to warm to RT and is stirred at RT for 30 min. The reaction mixture is poured into water and extracted with methylene chloride (2X). The combined extracts are dried and stripped to give, following purification by prep. TLC, (E)-3-octylthio-2-butenyl acetate. To the above acetate (0.44 g) dissolved in 15 ml of methylene chloride is added m-chloroperbenzoic acid (85%; 0.36 g). After about 30 min., the reaction mixture is washed with aq. NaHCO$_3$, dried, stripped and purified by prep. TLC to give (E)-3-octylsulfinyl-2-butenyl acetate (cpd. 9, Table A).

EXAMPLE 10

To a suspension of sodium hydride (1.48 g, 61.5 mmol) in 15 ml of dimethylformamide (DMF) is added a solution of 3-mercapto-1,2-propanediol (6.65 g, 61.5 mmol) in 5 ml of DMF at 5°. After addition is complete, the mixture is warmed to RT and then to 40° for 30 min. It is then cooled to 5° and 6-methoxyhexyl bromide (12.0 g, 61.5 mmol) is added dropwise. The mixture is stirred at RT for 2 hours and is then diluted with 10% aqueous NaH$_2$PO$_4$. It is extracted with ether, washed with water and brine and dried to give 3-methoxyhexylthio-1,2-propanediol.

Tosyl chloride (3.6 g, 18.9 mmol) is added in portions to a solution of the above diol (4.2 g, 18.9 mmol) in 15 ml of pyridine at 0°-5°. The mixture is stirred at 0° for 1 hour, then is stirred at RT for 1 hour. The reaction is quenched with water; extracted with ether; washed with 2N H$_2$SO$_4$, water, saturated NaHCO$_3$ and brine; and dried. The resulting tosylate (5.8 g, 17.4 mmol) is mixed with sodium hydroxide (0.69 g, 17.4 mmol), ether (20 ml) and water (25 ml), and to this mixture is added 3 drops of tricaprylylmethylammonium chloride (Aliquat 336, Aldrich). The mixture is stirred at RT for 4 hours, then extracted with ether, washed with brine and dried to give 2-(6-methoxyhexylthiomethyl)oxirane.

A mixture of the above epoxide (3.76 g, 18.0 mmol), potassium t-butoxide (0.4 g, 3.7 mmol) and hexamethylphosphoric amide (HMPA; 5 ml) is stirred at RT overnight. It is then diluted with water and extracted with ether to give 3-(6-methoxyhexylthio)-2-propenol.

To the above propenol (1.2 g) is added 2 ml of pyridine, followed by 1 ml of acetic anhydride and the mixture is stirred at RT until reaction is complete. The product is purified by prep. TLC to give 3-(6-methoxyhexylthio)-2-propenyl acetate.

Following the procedure of Example 2, the above acetate (0.45 g, 1.83 mmol) is reacted with silver fluoride (0.93 g, 7.3 mmol) and then iodine (0.58 g, 2.29 mmol), followed by triethylamine (2.6 ml, 18.3 mmol) to give, after purification by prep. TLC, 3-fluoro-3-(6-methoxyhexylthio)-2-propenyl acetate.

M-chloroperbenzoic acid (85%; 0.15 g, 0.75 mmol) is added to a solution of the above fluoropropenyl acetate (0.20 g, 0.75 mmol) in 3 ml of methylene chloride at 5°. The mixture is stirred for 15 min. and is then worked up with aq. Na$_2$SO$_4$ and sat'd aq. NaHCO$_3$, washed with brine and stripped of solvent to give 3-fluoro-3-(6-methoxyhexylsulfinyl)-2-propenyl acetate. The product is purified by prep. TLC on silica gel eluting with 50% ethyl acetate/hexane. The upper band is collected to give (E)-3-fluoro-3-(6-methoxyhexylsulfinyl)-2-propenyl acetate (cpd. 10, Table A).

NMR (CDCl$_3$) δ 5.78 (d of t, 1, J±, J=6.8 Hz, FC=CH trans), 4.74 (d of d, 2, J=2.8, J=6.5 Hz, =CH-CH$_2$O), 3.29 (s, 3, CH$_3$O), 2.90 (m, 2, CH$_2$S=O), 2.05 (s, $\overline{3}$, CH$_3$CO), 1.50 (m, 8, (CH$_2$)$_4$).

The lower band is collected to give (Z)-3-fluoro-3-(6-methoxyhexylsulfinyl)-2-propenyl acetate.

EXAMPLE 11

Following the procedure of Example 10, 2-butoxyethyltosylate (26.85 g, 98.7 mmol) and 3-mercapto-1,2-propanediol (10.68 g, 98.7 mmol) are reacted together to give 3-(2-butoxyethylthio)-1,2-propanediol, which diol (10.0 g, 52.5 mmol) is reacted with tosyl chloride (10.0 g) in pyridine. The tosylate (9.27 g, 25.6 mmol) is reacted with NaOH (1.02 g, 25.6 mmol) to give 2-(2-butoxyethylthiomethyl)oxirane. The oxirane (1.0 g, 5.26 mmol) and potassium t-butoxide (0.18 g, 1.58 mmol) are reacted together to give 3-(2-butoxyethylthio)-2-propenol, which propenol (4.72 g, 25.0 mmol) is reacted with acetic anhydride to give 3-(2-butoxyethylthio)-2-propenyl acetate.

Following the procedure of Example 2, the above acetate (1.18 g, 5.0 mmol) is reacted with silver fluoride (2.58 g, 20.0 mmol) and then iodine (1.57 g, 6.2 mmol), followed by triethylamine (6.96 ml) to give 3-fluoro-3-(2-butoxyethylthio)2-propenyl acetate.

The above fluoropropenyl acetate (0.65 g, 2.6 mmol) is reacted with m-chloroperbenzoic acid (0.58 g, 2.9 mmol) following Example 3 procedures to give, upon collection of the upper prep. TLC band, (E)-3-fluoro-3-(2-butoxyethylsulfinyl)-2-propenyl acetate (cpd. 11, Table A).

NMR (CDCl$_3$) δ 5.79 (d of t, 1, J=34.5, J=7.0 Hz, FC=CH trans), 4.73 (d of d, 2, J=2.5, J=7.0 Hz, =CH-CH$_2$O), 3.79 (t, 2, J=6.0 Hz, OCH$_2$CH$_2$S=O), 3.43 (t, $\overline{2}$, J=6.0 Hz, OCH$_2$CH$_2$), 3.07 (t, $\overline{2}$, J=6.0 Hz, OCH$_2$CH$_2$S=O), 2.05 (s, $\overline{3}$, CH$_3$CO), 1.4 (m, 4, (CH$_2$)$_2$), 0.88 (t, $\overline{3}$, J=6.0 Hz, CH$_3$).

EXAMPLE 12

Following the procedure of Example 1, each of 4-methyl-3-pentenethiol, 3-trifluoromethyl-2-butenethiol, 3,3-dichloro2-propenethiol and 2-phenylethanethiol is reacted with methyl propiolate to give, respectively, 3-(4-methyl-3-pentenylthio)-2-propenyl acetate, 3-(3-trifluoromethyl-2-butenylthio)-2-propenyl acetate, 3-(3,3-dichloro-2-propenylthio)-2-propenyl acetate, and 3-(2-phenylethylthio)-2-propenyl acetate.

Following the procedure of Example 2, each of the above acetates is reacted with silver fluoride and iodine followed by triethylamine to give, respectively, 3-fluoro-3-(4-methyl-3-pentenylthio)-2-propenyl acetate, 3-fluoro-3-(3-trifluoromethyl-2-butenylthio)-2-propenyl acetate, 3-fluoro-3-(3,3-dichloro-2-propenylthio)-2-propenyl acetate, and 3-fluoro-3-(2-phenylethylthio)-2-propenyl acetate.

Following the procedure of Example 3, each of the above fluoropropenyl acetates is reacted with m-chloroperbenzoic acid to give, respectively, (E)-3-fluoro-3-(4-methyl-3-pentenylsulfinyl)-2-propenyl acetate (cpd. 12, Table A), NMR (CDCl$_3$) δ 5.78 (d of t, 1, J=34, J=6.5 Hz, CF=CH trans), 5.07 (m, 1, (CH$_3$)$_2$C=CH), 4.73 (d of d, J=2.5, J=7.0 Hz, CH$_2$O), 2.88 (m, 2, CH$_2$S=O), 2.47 (m, 2, (CH$_3$)$_2$-C=CH), 2.07 (s, 3, CH$_3$CO), 1.68 (s, 3, CH$_3$C=C), 1.65 (s, $\overline{3}$, CH$_3$C=C);

(E)-3-fluoro-3-(3-trifluoromethyl-2-butenylsulfinyl)2-propenyl acetate (cpd. 13, Table A), NMR (CDCl$_3$) δ 6.07 (t, 1, J=6.5 Hz, CH$_3$CF$_3$C=CH), 5.83 (d of t, 1, J=35, J=6.5 Hz, CH=CF trans), 4.73 (d of d, 2, J=3.0, J=7.5 Hz, CH$_2$O), 3.70 (m, 2, CH$_2$S=O), 2.10 (s, 3, CH$_3$CO), 1.88 (s, 3, CH$_3$C=);

(E)-3-fluoro-3-(3,3-dichloro-2-propenylsulfinyl)-2-propenyl acetate (cpd. 14, Table A), NMR (CDCl$_3$) δ 5.92 (t, 1, J=8.0 Hz, Cl$_2$C=CH), 5.83 (d of t, 1, J=35, J=7 Hz, CF=CH trans), 4.78 (d of d, 2, J=2.5, J=6.5 Hz, CH$_2$O), 3.80 (m, 2, CH$_2$S=O), 2.07 (s, 3, CH$_3$C=O); and (E)-3-fluoro-3-(2-phenylethylsulfinyl)-2-propenyl acetate (cpd. 15, Table A).

EXAMPLE 13

To a solution of 3-butylthio-2-propenyl acetate (1.0 g, 5.3 mmol) in 25 ml of methylene chloride at 5° is added dropwise iodine monochloride (0.86 g, 5.3 mmol) over a period of 20 min. The mixture is stirred at RT for 2 hours, after which it is cooled to 5° and m-chloroperbenzoic acid (85%; 1.08 g, 5.3 mmol) is added in four portions over 2 min. The reaction mixture is stirred at RT for 15 min., and then triethylamine (3.7 ml, 26.5 mmol) is added. After stirring at RT overnight, the mixture is diluted in chloroform; washed with 2NH$_2$SO$_4$, water, saturated NaHCO$_3$, and brine; and dried. The crude product is purified by prep. TLC on silica gel eluting with 40% ethyl acetate/hexane. The upper band is collected to yield (Z)-3-chloro-3-butylsulfinyl2-propenyl acetate (cpd. 16, Table A).

NMR (CDCl$_3$) δ 6.60 (t, 1, J=6.2 Hz, ClC=CH), 4.82 (d, 2, J=6.2 Hz, CH$_2$O), 2.82 (m, 2, CH$_2$S=O), 2.03 (s, 3, CH$_3$C=O), 1.53 (m, 4, (CH$_2$)$_4$), 0.94 (m, 3, CH$_3$).

Following the above procedure, each of 3-(3-trifluoromethyl-2-butenylthio)-2-propenyl acetate and 3-(3,3-dichloro-2-propenylthio)-2-propenyl acetate is reacted with iodine monochloride, followed by m-chloroperbenzoic acid and triethylamine to give, respectively, (Z)-3-chloro-3-(3-trifluoromethyl-2-butenylsulfinyl)2-propenyl acetate (cpd. 17, Table A),

[NMR (CDCl$_3$) δ 6.62 (t, 1, J=6.0 Hz ClC=CH), 6.07 (m, 1, CF$_3$C=CH), 4.85 (d, 2, J=6.0 Hz, CH$_2$O), 3.75 (m, 2, CH$_2$S=O), 2.07 (s, 3, CH$_3$C=O), 1.87 (s, 3, CH$_3$C=C)]; and (Z)-3-chloro-3-(3,3-dichloro-2-propenylsulfinyl)-2-propenyl acetate (cpd. 18, Table A),

[NMR (CDCl$_3$) δ 6.67 (t, 1, J=6.5 Hz, O=SC=CH), 5.98 (t, 1, J=7.5 Hz, Cl$_2$C=CH), 4.91 (d, 2, J=6.5 Hz, CH$_2$O), 3.78 (d, 1, J=7.5 Hz, CH—S=O), 3.75 (d, 1, J=7.5 Hz, CH—S=O), 2.10 (s, 3, CH$_3$C=O)].

EXAMPLE 14

To a solution of 3-hexylthio-2-propenyl acetate (1.3 g, 6.0 mmol) in 10 ml of ether cooled to -10° is added bromine (1.05 g, 0.34 ml, 6.6 mmol). The mixture is stirred at ambient temperature for 30 min., then cooled to 0° and triethylamine (3.0 g, 4.18 ml, 30.0 mmol) is added. The reaction mixture is stirred overnight at RT, then diluted with water and extracted with hexane. The extract is washed with 2N H$_2$SO$_4$, water, saturated NaHCO$_3$ and brine and is dried. The crude product is purified by prep. TLC on silica gel eluting with 20% ethyl acetate/hexane. The upper band is collected to give 3-bromo-3-hexylthio-2-propenyl acetate. The lower band is collected to give 2-bromo-3-hexylthio-2propenyl acetate.

Following the procedure of Example 3, each of 3-bromo3-hexylthio-2-propenyl acetate and 2-bromo-3-hexylthio-2-propenyl acetate is reacted with m-chloroperbenzoic acid to give, on collection of the upper band, (Z)-3-bromo-3-hexylsulfinyl-2-propenyl acetate (cpd. 19, Table A), and (Z)-2-bromo-3-hexylsulfinyl-2-propenyl acetate (cpd. 20, Table A).

EXAMPLE 15

To a mixture of potassium thiocyanate (5.07 g, 51.7 mmol) in 30 ml of dimethylformamide (DMF) is added 1-bromooctane (5.0 g, 4.5 ml, 25.8 mmol). The mixture is stirred at 45° for 1.5 hours. It is then cooled to 0° and water and ether are added. The ether layer is washed with water and brine and stripped to give octylthiocyanate.

To a solution of 2-propynol (0.65 g/0.68 ml, 11.7 mmol) in 25 ml of tetrahydrofuran (THF), cooled to -60°, is slowly added butyllithium in hexane (14.6 ml, 23.3 mmol) over 5 min. About 5 ml of HMPA is added and the mixture is warmed to -20° and stirred for 5 min. The mixture is then cooled again to -60° and octylthiocyanate (2.0 g, 11.7 mmol) in 3 ml of THF is added over 1 min. The mixture is allowed to warm to RT over 1 hour and is stirred at RT for an additional hour. It is then cooled to -10° and quenched with water. The reaction mixture is diluted with ether, washed with water and brine and dried to give 3-octylthio-2-propynol.

Acetic anhydride (1.88 g/1.82 ml, 18.4 mmol), 3-octylthio-2-propynol (2.46 g, 12.3 mmol) and pyridine (2.47 ml, 31.0 mmol) are added together at 10°, and the resulting mixture is stirred at RT for 2 hours. It is then cooled to 10° and 10 ml of water is added. After stirring for 10 min., the reaction mixture is diluted with ether and water, washed with cold 2N H$_2$SO$_4$ and NaHCO$_3$ and stripped to give, after purification by prep. TLC, 3-octylthio-2-propynyl acetate.

To a solution of the above propynyl acetate (0.2 g, 0.825 mmol) in 10 ml of carbon tetrachloride at 10° is added chlorine in CCl$_4$ (0.79M, 1.04 ml, 0.825 mmol). The mixture is stirred at RT for about 1 hour, after which it is diluted with ether and then stripped of solvent to give 2,3-dichloro3-octylthio-2-propenyl acetate.

M-chloroperbenzoic acid (85%; 0.13 g, 0.638 mmol) is added to a cooled (10°) solution of the above dichloropropenyl acetate (0.2 g, 0.638 mmol) in 5 ml of methylene chloride. The mixture is stirred at 10° for 1 hour, after which it is diluted with ether, washed with water and brine and stripped. The crude product is purified by prep. TLC (silica gel eluting with 20% ethylacetate/hexane) and the upper band is collected to give (Z)-2,3-dichloro-3-octylsulfinyl-2-propenyl acetate (cpd. 21, Table A).

NMR (CDCl$_3$) δ 4.9 (2d, 2, J=13.5, CH$_2$O), 2.85 (m, 2, CH$_2$—S=O), 2.1 (s, 3, COCH$_3$), 1.28 (m, 12, (CH$_2$)$_6$), 0.86 (m, 3, CH$_2$CH$_3$).

EXAMPLE 16

A mixture of 3-mercapto-1,2-propanediol (10.8 g), 3,3-dimethyl-1-butene (9.6 g) and 2,2'-azobis(2-methylpropionitrile) (0.5 g) is heated under reflux with vigorous stirring for 20 hours, then is diluted with hexane, extracted with water and stripped to give 3-(3,3-dimethylbutylthio)-1,2propanediol.

Following the procedure of Example 10, the above diol (15.4 g, 80.0 mmol) is reacted with tosyl chloride (28.0 g) to give the corresponding tosylate, which is reacted with NaOH (1.7 g, 42.5 mmol) to give 3,3-dimethylbutylthiomethyloxirane. The oxirane and potassium t-butoxide (3.0 g) are reacted together to give 3-(3,3-dimethylbutylthio)-2-propenol, which is reacted with acetic anhydride (10 ml) to give, after purification, 3-(3,3-dimethylbutylthio)-2-propenyl acetate.

Following the procedure of Example 2, the above acetate (5.4 g) is reacted with silver fluoride (12.7 g) and iodine (8.0 g), followed by triethylamine (12.5 ml) to give 3-fluoro-3-(3,3-dimethylbutylthio)-2-propenyl acetate.

Following the procedure of Example 3, the above fluoropropenyl acetate (4.0 g) is reacted with m-chloroperbenzoic acid (3.68 g) to give, upon collection of the upper prep. TLC band, (E)-3-fluoro-3-(3,3-dimethylbutylsulfinyl)-2-propenyl acetate (cpd. 22, Table A).

NMR (CDCl$_3$) δ 5.84 (d of t, 1, J=35, J=6.8 Hz, trans CF=CH), 4.81 (d of d, 2, J=2.4, J6.8 Hz, CF=CH-CH$_2$O), 2.92 (m, 2, CH$_2$S=O), 2.08 (s, 3, COCH$_3$), 1.64 (m, 2, CH$_2$CH$_2$S=O), 0.96 (s, 9, C(CH$_3$)$_3$).

EXAMPLE 17

Tert-butyl hypochlorite (2.06 g, 19.0 mmol) is added dropwise at −50° to a solution of 3-hexylthio-1-propene (3.0 g, 19.0 mmol) in 20 ml of methylene chloride. The mixture is allowed to warm to RT and is then stripped of solvent to give 3-hexylthio-2-propenyl chloride.

3-Hexylthio-2-propenyl chloride is added to a solution of diisopropyl ethyl amine (3.68 g, 28.5 mmol) in 20 ml of methanol. The mixture is stirred overnight at RT. It is then diluted with hexane, washed with water and with brine and is stripped. The crude product is purified by prep. TLC to give 3-methoxy-1-hexylthio-1-propene.

NMR (CDCl$_3$) δ6.28 (d, 1, J=15 Hz, CH=CHCH$_2$), 5.59 (d of t, J=15, J=6.0 Hz, CH=CHCH$_2$), 3.92 (d, 2, J=6 Hz, CH$_2$OCH$_3$), 3.35 (s, 3, OCH$_3$), 2.70 (m, 2, CH$_2$S), 1.39 (m, 8, (CH$_2$)$_4$), 0.96 (m, 3, CH$_3$).

Silver (I) fluoride (2.0 g, 15.7 mmol) is added to a solution of the above propene (0.74 g, 3.9 mmol) in 20 ml of acetonitrile, and the mixture is stirred at RT for 30 min. Iodine (1.24 g, 4.9 mmol) is then added, followed after 30 min. by the addition of triethylamine (3.9 g, 39.0 mmol). The mixture is stirred at RT for 4 hours, then filtered, washed with ether and stripped of solvent. The residue is diluted with chloroform, filtered and stripped to give, after purification by prep. TLC, 3-methoxy-1-fluoro-1-hexylthio-1-propene.

NMR (CDCl$_3$) δ 4.8–6.0 (m, 1,.CH=CH), 4.0 (m, 2, CH$_2$OCH$_3$), 3.30 (s, 3, OCH$_3$), 2.70 (m, 2, CH$_2$S), 1.30 (m, 8, (CH$_2$)$_4$), 0.88 (m, 3, CH$_3$).

Following the procedure of Example 3, 3-methoxy-1-fluoro-1-hexylthio-1-propene (0.26 g, 1.3 mmol) is reacted with m-chloroperbenzoic acid (0.28 g, 1.4 mmol) to give, upon collection of the upper prep. TLC band, (E)-3-methoxy-1-fluoro-1-hexylsulfinyl-1-propene (cpd. 23, Table A).

NMR (CDCl$_3$) δ 5.80 (d of t, 1, J=35, J=6.8 Hz, trans CF=CH), 4.12 (d of d, 2, J=2.4, J=7.0 Hz, CH$_2$O), 3.34 (s, 3, CH$_3$O), 2.90 (m, 2, CH$_2$S=O).

EXAMPLE 18

Following the procedure of Example 17, 3-hexylthio-2-propenyl chloride is reacted with each of 2-chloroethanol, 2-methoxyethanol, 2-propenol and 1-hydroxy-2-propanone to give the corresponding 3-substituted 1-hexylthio-1-propenes, each of which is then treated with silver fluoride, iodine and triethylamine to give the corresponding 1-fluoro-1-hexylthio-1-propenes. Each fluoropropene is then reacted with m-chloroperbenzoic acid and purified by prep. TLC to give, respectively, (E)-3-(2-chloroethoxy)-1-fluoro-1-hexylsulfinyl-1-propene (cpd. 24, Table A), (E)-3-(2-methoxyethoxy)-1-fluoro-1-hexylsulfinyl-1-propene (cpd. 25, Table A), (E)-3-allyloxy-1-fluoro-1-hexylsulfinyl-1-propene (cpd. 26, Table A), and (E)-3-aceto-nyloxy-1-fluoro-1-hexylsulfinyl-1-propene (cpd. 27, Table A).

EXAMPLE 19

Compounds of the present invention were tested for contact activity on the tomato hornworm, Manduca sexta, in the following manner:

Twenty 0–24 hr. IIIrd instar M. sexta larvae were treated with 1 μl of the test compound in acetone at different dosage rates by application to the dorsum of the thorax. Larvae are held individually in 1 oz. plastic cups provided with artificial food and incubated at 27°. The larvae are scored after each molt to the subsequent instar until they have reached the Vth instar or have died. The effect is expressed as ED$_{50}$, which is the dosage, in μg per insect, required to exhibit scoreable effects in 50% of the test insects. Scoreable effects are those effects which affect larval development and metamorphosis to the point where the larva would not be able to develop to the next larval stage or to adulthood. These can include direct toxicity, precocious development of pupal cuticle, premature prepupal behavior, chitin inhibition, molting difficulties and lack of larval growth. For each of the compounds (E)-3-fluoro-3-hexylsulfinyl2-propenyl acetate, (E)-3-fluoro-3-hexyl-sulfinyl-2-propenol, (E)-3-fluoro-3-hexylsulfinyl-2-propenyl formate, and (E)-3-fluoro-3-(2-butoxyethylsulfinyl)-2-propenyl acetate the ED$_{50}$ was less than 2.0 μg per insect.

EXAMPLE 20

Twenty 0–24 hr. IIIrd instar larvae of Spodoptera exigua (beet armyworm) were treated with 1 μl of the test compound in acetone at different dosage rates by application to the dorsum of the thorax. The treated larvae are held in individual compartments provided with food and are incubated for three days at 25° after which observations are made. The effect is expressed as ED$_{50}$ as in Example 18. For each of the compounds (E)-3-fluoro-3-hexylsulfinyl-2-propenyl acetate, (E)-3-fluoro3-hexylsulfinyl-2-propenol, (E)-3-fluoro-3-hexyl-sulfinyl-2-propenyl formate, and (E)-3-fluoro-3-(2-butoxyethylsulfinyl)-2-propenyl acetate the ED$_{50}$ was less than 2.0 μg per insect.

EXAMPLE 21

To a slurry of sodium hydride (125 mg, 5.2 mmol) in 5 ml of THF and 2 ml of HMPA under N$_2$ is added dimethylcarbamoyl chloride (0.37 ml, 430 mg, 4.0 mmol). The slurry is cooled in an ice bath and 3-fluoro-3-hexylthio-2-propen-1-ol (450 mg, 2.34 mmol) is added gradually. After 1 hour, the mixture is cautiously poured into water, extracted with ether and stripped to give 3-fluoro-3-hexylthio-2-propenyl dimethylcarbamate.

To the above carbamate is added a solution of m-chloroperbenzoic acid (431 mg, 2.5 mmol) in 10 ml of methylene chloride. After 15 min, the reaction mixture is extracted with KHCO$_3$ and Na$_2$SO$_3$ and stripped. The product is purified by prep. TLC eluting with ethyl acetate (neat). The upper band is collected to give (E)-3-fluoro-3-hexylsulfinyl-2-propenyl dimethylcarbamate (cpd. 28, Table A).

NMR (CDCl$_3$) δ 5.87 (d of t, 1, J=35.8, J=6.6 Hz, trans CH=CF), 4.82 (d of d, 2, J=6.8, J=2.6 Hz, CH$_2$O), 2.92 (s, 6, (CH$_3$)$_2$N), 2.90 (m, 2, CH$_2$S=O), 1.35 (m, 8, (CH$_2$)$_4$), 0.90 (t, 3, J=5.9 Hz, CH$_2$CH$_3$).

The lower band is collected to give (Z)-3-fluoro-3-hexylsulfinyl-2-propenyl dimethylcarbamate.

TABLE A $$R^1-\underset{O}{\underset{\|}{S}}-\underset{Y}{\overset{X}{C}}=C-CH_2-O-R^2 \quad (C')$$

| Cpd | Isomer | R$^1$ | X | Y | R$^2$ |
|---|---|---|---|---|---|
| 1 | E | CH$_3$—CH$_2$—CH$_2$—CH$_2$—CH$_2$—CH$_2$ | F | H | —C(=O)—CH$_3$ |
| 2 | E | CH$_3$—CH$_2$—CH$_2$—CH$_2$—CH$_2$—CH$_2$ | F | H | H |
| 3 | E | CH$_3$—CH$_2$—CH$_2$—CH$_2$—CH$_2$—CH$_2$ | F | H | —C(=O)H |
| 4 | E | CH$_3$—CH$_2$—CH$_2$—CH$_2$—CH$_2$—CH$_2$ | F | H | —C(=O)CH$_2$—CH$_2$—CH$_3$ |
| 5 | E | CH$_3$—CH$_2$—CH$_2$—CH$_2$—CH$_2$—CH$_2$ | F | H | —C(=O)O—CH$_2$—CH$_2$ |
| 6 | E | CH$_3$—CH$_2$—CH$_2$—CH$_2$—CH$_2$—CH$_2$—CH$_2$ | F | H | —C(=O)CH$_3$ |
| 7 | E | CH$_3$—CH$_2$—CH$_2$—CH$_2$ | F | H | —C(=O)CH$_3$ |
| 8 | E | CH$_3$—CH$_2$—CH$_2$—CH$_2$—CH$_2$ | F | H | —C(=O)CH$_3$ |
| 9 | E | CH$_3$—CH$_2$—CH$_2$—CH$_2$—CH$_2$—CH$_2$—CH$_2$—CH$_2$ | CH$_3$ | H | —C(=O)CH$_3$ |
| 10 | E | CH$_3$—O—CH$_2$—CH$_2$—CH$_2$—CH$_2$—CH$_2$—CH$_2$ | F | H | —C(=O)CH$_3$ |
| 11 | E | CH$_3$—CH$_2$—CH$_2$—CH$_2$—O—CH$_2$—CH$_2$ | F | H | —C(=O)CH$_3$ |
| 12 | E | CH$_3$—C(CH$_3$)=CH—CH$_2$—CH$_2$ | F | H | —C(=O)CH$_3$ |
| 13 | E | CH$_3$—C(CF$_3$)=CH—CH$_2$ | F | H | —C(=O)CH$_3$ |
| 14 | E | C(Cl)$_2$=CH—CH$_2$ | F | H | —C(=O)CH$_3$ |
| 15 | E | C$_6$H$_5$—CH$_2$—CH$_2$ | F | H | —C(=O)CH$_3$ |
| 16 | Z | CH$_3$—CH$_2$—CH$_2$—CH$_2$ | Cl | H | —C(=O)CH$_3$ |
| 17 | Z | CH$_3$—C(CF$_3$)=CH—CH$_2$ | Cl | H | —C(=O)CH$_3$ |
| 18 | Z | C(Cl)$_2$=CH—CH$_2$ | Cl | H | —C(=O)CH$_3$ |

TABLE A-continued $$R^1-S(=O)-C(X)=C(Y)-CH_2-O-R^2 \quad (C')$$

| Cpd | Isomer | R$^1$ | X | Y | R$^2$ |
|---|---|---|---|---|---|
| 19 | Z | CH$_3$—CH$_2$—CH$_2$—CH$_2$—CH$_2$—CH$_2$ | Br | H | —C(=O)CH$_3$ |
| 20 | Z | CH$_3$—CH$_2$—CH$_2$—CH$_2$—CH$_2$—CH$_2$ | H | Br | —C(=O)CH$_3$ |
| 21 | Z | CH$_3$—CH$_2$—CH$_2$—CH$_2$—CH$_2$—CH$_2$—CH$_2$—CH$_2$ | Cl | Cl | —C(=O)CH$_3$ |
| 22 | E | CH$_3$—C(CH$_3$)$_2$—CH$_2$—CH$_2$ | F | H | —C(=O)CH$_3$ |
| 23 | E | CH$_3$—CH$_2$—CH$_2$—CH$_2$—CH$_2$—CH$_2$ | F | H | CH$_3$ |
| 24 | E | CH$_3$—CH$_2$—CH$_2$—CH$_2$—CH$_2$—CH$_2$ | F | H | CH$_2$—CH$_2$Cl |
| 25 | E | CH$_3$—CH$_2$—CH$_2$—CH$_2$—CH$_2$—CH$_2$ | F | H | CH$_2$—CH$_2$—O—CH$_3$ |
| 26 | E | CH$_3$—CH$_2$—CH$_2$—CH$_2$—CH$_2$—CH$_2$ | F | H | CH$_2$—CH=CH$_2$ |
| 27 | E | CH$_3$—CH$_2$—CH$_2$—CH$_2$—CH$_2$—CH$_2$ | F | H | CH$_2$—C(=O)—CH$_3$ |
| 28 | E | CH$_3$—CH$_2$—CH$_2$—CH$_2$—CH$_2$—CH$_2$ | F | H | —C(=O)—N(CH$_3$)$_2$ |

What is claimed is:

1. A compound of the following formula (A):

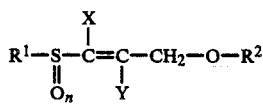

(A)

wherein, n is zero, one or two;

R$^1$ is lower alkyl of 1–8 carbon atoms, lower haloalkyl of 1–8 carbon atoms, lower alkenyl of 2–8 carbon atoms, lower haloalkenyl of 2–8 carbon atoms, lower alkoxyalkyl of 2–10 carbon atoms or phenylalkyl;

R$^2$ is hydrogen, lower alkyl of 1–8 carbon atoms, lower haloalkyl of 1–8 carbon atoms, lower alkoxyalkyl of 2–10 carbon atoms, lower acylalkyl of 3–10 carbon atoms, lower alkenyl of 2–8 carbon atoms, lower haloalkenyl of 2–8 carbon atoms, lower alkynyl of 2–8 carbon atoms, lower acyl of 2–8 carbon atoms or lower alkoxycarbonyl of 2–8 carbon atoms;

X is hydrogen, lower alkyl of 1–8 carbon atoms, lower haloalkyl of 1–8 carbon atoms or halogen; and Y is hydrogen or halogen; provided that:

(a) when n is zero R$^1$ is 3-methyl-2-butenyl, R$^2$ is hydrogen and Y is hydrogen, then X is other than methyl; or (b) when R$^2$ is hydrogen or lower acyl and Y is hydrogen, then X is other than hydrogen.

2. A compound according to claim 1 wherein R$^2$ is hydrogen, lower alkyl of 1–8 carbon atoms, lower acyl of 2–8 carbon atoms or lower alkoxycarbonyl of 2–14 8 carbon atoms and X is lower alkyl of 1–8 carbon atoms or halogen.

3. A compound according to claim 2 wherein R$^1$ is lower alkyl of 1–8 carbon atoms, lower alkenyl of 2–8 carbon atoms or lower alkoxyalkyl of 2–8 carbon atoms and Y is hydrogen.

4. A compound of the following formula, according to claim 3;

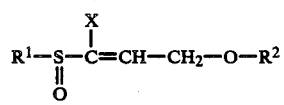

5. A compound according to claim 4 wherein R$^1$ is pentyl, hexyl or heptyl; R$^2$ is hydrogen, formyl, acetyl or butyryl; and X is chloro or fluoro.

6. A compound according to claim 5 wherein R$^1$ is hexyl and X is fluoro.

7. The compound (E)-3-fluoro-3-hexylsulfinyl-2-propenyl formate, according to claim 6.

8. The compound (E)-3-fluoro-3-hexylsulfinyl-2-propenyl acetate, according to claim 6.

9. The compound (E)-3-fluoro-3-hexylsulfinyl-2-propenyl butyrate, according to claim 6.

10. A compound according to claim 4 wherein R$^1$ is 6-methoxyhexyl or 2-(1-butoxy)ethyl, R$^2$ is acetyl and X is fluoro.

11. A method for the control of insects at an immature stage of growth which comprises applying to the immature insect or its locus in an insect controlling amount a compound of the following formula (A):

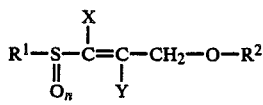

(A)

wherein, n is zero, one or two;

R[1] is lower alkyl of 1-8 carbon atoms, lower haloalkyl of 1-8 carbon atoms, lower alkenyl of 2-8 carbon atoms, lower haloalkenyl of 2-8 carbon atoms, lower alkoxyalkyl of 2-10 carbon atoms or phenylalkyl;

R[2] is hydrogen, lower alkyl of 1-8 carbon atoms, lower haloalkyl of 1-8 carbon atoms, lower alkoxyalkyl of 2-10 carbon atoms, lower acylalkyl of 3-10 carbon atoms, lower alkenyl of 2-8 carbon atoms, lower haloalkenyl of 2-8 carbon atoms, lower alkynyl of 2-8 carbon atoms, lower acyl of 2-8 carbon atoms or lower alkoxycarbonyl of 2-8 carbon atoms;

X is hydrogen, lower alkyl of 1-8 carbon atoms, lower haloalkyl of 1-8 carbon atoms or halogen; and Y is hydrogen or halogen.

12. The method according to claim 11 wherein R[2] is hydrogen, lower alkyl of 1-8 carbon atoms, lower acyl of 2-8 carbon atoms, or lower alkoxycarbonyl of 2-8 carbon atoms and X is lower alkyl of 1-8 carbon atoms or halogen.

13. The method according to claim 12 wherein R[1] is lower alkyl of 1-8 carbon atoms, lower alkenyl of 2-8 carbon atoms or lower alkoxyalkyl or 2-8 carbon atoms and Y is hydrogen.

14. The method according to claim 13 with a compound of the following formula:

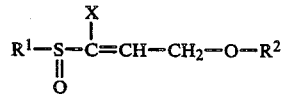

15. The method according to claim 14 wherein R[1] is pentyl, hexyl or heptyl; R[2] is hydrogen, formyl, acetyl or butyryl; and X is chloro or fluoro.

16. The method according to claim 15 wherein R[1] is hexyl and X is fluoro.

17. The method according to claim 16 wherein the compound is (E)-3-fluoro-3-hexylsulfinyl-2-propenyl acetate.

18. The method according to claim 14 wherein R[1] is 6-methoxyhexyl or 2-(1-butoxy)ethyl, R[2] is acetyl and X is fluoro.

19. The method according to claim 11 wherein the insect is from the order Lepidoptera.

20. The method according to claim 19 wherein the immature stage is the larval stage.

* * * * *